US009499453B2

(12) United States Patent
Tasaka

(10) Patent No.: US 9,499,453 B2
(45) Date of Patent: Nov. 22, 2016

(54) CATALYST FILLING APPARATUS OF BUBBLE COLUMN SLURRY BED REACTOR AND CATALYST FILLING METHOD OF BUBBLE COLUMN SLURRY BED REACTOR

(71) Applicants:Japan Oil, Gas and Metals National Corporation, Tokyo (JP); Inpex Corporation, Tokyo (JP); JX Nippon Oil & Energy Corporation, Tokyo (JP); Japan Petroleum Exploration Co., Ltd., Tokyo (JP); Cosmo Oil Co., Ltd., Tokyo (JP); Nippon Steel & Sumikin Engineering Co., Ltd., Tokyo (JP)

(72) Inventor: Kazuhiko Tasaka, Tokyo (JP)

(73) Assignees: Japan Oil, Gas and Metals National Corporation, Tokyo (JP); INPEX CORPORATION, Tokyo (JP); JX Nippon Oil & Energy Corporation, Tokyo (JP); Japan Petroleum Exploration Co., Ltd., Tokyo (JP); COSMO OIL CO., LTD., Tokyo (JP); NIPPON STEEL & SUMKIN ENGINEERING CO., LTD., Tokyo (JP)

( * ) Notice: Subject to any disclaimer, the term of this patent is extended or adjusted under 35 U.S.C. 154(b) by 0 days.

(21) Appl. No.: 14/387,560

(22) PCT Filed: Mar. 27, 2013

(86) PCT No.: PCT/JP2013/058926
§ 371 (c)(1),
(2) Date: Sep. 24, 2014

(87) PCT Pub. No.: WO2013/146849
PCT Pub. Date: Oct. 3, 2013

(65) Prior Publication Data
US 2015/0064070 A1     Mar. 5, 2015

(30) Foreign Application Priority Data
Mar. 28, 2012   (JP) .................. 2012-074758

(51) Int. Cl.
*C07C 1/04*     (2006.01)
*B01J 8/20*     (2006.01)
(Continued)

(52) U.S. Cl.
CPC ................ *C07C 1/0415* (2013.01); *B01J 8/20* (2013.01); *B01J 8/222* (2013.01); *B01J 8/228* (2013.01);
(Continued)

(58) Field of Classification Search
CPC .......... C07C 1/04; C07C 1/0415; B01J 8/20; B01J 8/222; B01J 8/228; C10G 2/342
USPC ......................................... 422/140; 502/100
See application file for complete search history.

(56) References Cited

U.S. PATENT DOCUMENTS

| 2,891,907 A | 6/1959 | Jewell |
| 5,770,629 A | 6/1998 | Degeorge et al. |

(Continued)

FOREIGN PATENT DOCUMENTS

| CA | 2793824 A1 | 10/2011 |
| CN | 1326495 A | 12/2001 |

(Continued)

OTHER PUBLICATIONS

Hamelinck et al, "Production of FT transportation fuels from biomass; technical options, process analysis and optimisation, and development potential," Energy, vol. 29, pp. 1743-1771 (2004).

(Continued)

*Primary Examiner* — Walter D Griffin
*Assistant Examiner* — Huy-Tram Nguyen
(74) *Attorney, Agent, or Firm* — Panitch Schwarze Belisario & Nadel LLP

(57) ABSTRACT

A catalyst filling apparatus is for a bubble column slurry bed reactor for the FT synthesis reaction. The apparatus includes: a slurry preparation tank installed adjacent to the reactor and configured to prepare a slurry S from a FT synthesis reaction catalyst and a slurry preparation oil; an upper part communication line configured to direct the slurry from the reactor to the slurry preparation tank; a lower part communication line configured to direct the slurry in the slurry preparation tank to the reactor; and a pressure equalizing line configured to communicate the reactor with the slurry preparation tank. The upper part communication line is downwardly inclined from the reactor toward the slurry preparation tank, and the lower part communication line is upwardly inclined from the reactor toward the slurry preparation tank. An inert gas introduction device is provided on the slurry preparation tank.

2 Claims, 2 Drawing Sheets

(51) Int. Cl.
*C10G 2/00* (2006.01)
*B01J 8/22* (2006.01)
(52) U.S. Cl.
CPC ........ *C10G 2/342* (2013.01); *B01J 2208/0061* (2013.01); *B01J 2208/00141* (2013.01); *B01J 2219/00009* (2013.01)

(56) References Cited

U.S. PATENT DOCUMENTS

| | | | |
|---|---|---|---|
| 6,090,859 A | 7/2000 | Howsmon et al. | |
| 6,800,664 B1 | 10/2004 | Espinoza et al. | |
| 6,974,844 B2 | 12/2005 | Steynberg | |
| 8,057,744 B2* | 11/2011 | Onishi | B01J 8/007 422/140 |
| 2005/0027020 A1 | 2/2005 | Steynberg | |
| 2009/0003126 A1 | 1/2009 | Hassan et al. | |
| 2009/0069450 A1 | 3/2009 | Ibsen et al. | |
| 2012/0190535 A1* | 7/2012 | Onishi | B01J 33/00 502/150 |

FOREIGN PATENT DOCUMENTS

| | | | | |
|---|---|---|---|---|
| CN | 101809122 A | 8/2010 | | |
| CN | 102165038 A | 8/2011 | | |
| JP | 2002-530472 A | 9/2002 | | |
| JP | 2004-323626 A | 11/2004 | | |
| JP | 2005-517698 A | 6/2005 | | |
| JP | 2011-206741 A | 10/2011 | | |
| WO | 9414573 A1 | 7/1994 | | |
| WO | 9850489 A1 | 11/1998 | | |
| WO | 0029513 A1 | 5/2000 | | |
| WO | 03068715 A1 | 8/2003 | | |
| WO | WO 2007069317 A1 * | 6/2007 | ............. B01J 8/007 |
| WO | 2011024651 A1 | 3/2011 | | |
| WO | WO 2011024651 A1 * | 3/2011 | ............. B01J 33/00 |

OTHER PUBLICATIONS

Int'l Search Report issued May 21, 2013 in Int'l Application No. PCT/JP2013/058926.
Office Action issued Jun. 26, 2015 in CN Application No. 201380016375.0.
Office Action issued Jul. 8, 2015 in AU Application No. 2013241357.
Extended Search Report issued Feb. 8, 2016 in EP Application No. 13769386.7.

* cited by examiner

CATALYST FILLING APPARATUS OF BUBBLE COLUMN SLURRY BED REACTOR AND CATALYST FILLING METHOD OF BUBBLE COLUMN SLURRY BED REACTOR

CROSS-REFERENCE TO RELATED APPLICATION

This application is a Section 371 of International Application No. PCT/JP2013/058926, filed Mar. 27, 2013, which was published in the Japanese language on Oct. 3, 2013, under International Publication No. WO 2013/146849A1, and the disclosure of which is incorporated herein by reference.

TECHNICAL FIELD

The present invention relates to a catalyst filling apparatus of a bubble column slurry bed reactor and a catalyst filling method of a bubble column slurry bed reactor.

Priority is claimed on Japanese Patent Application No. 2012-074758, filed Mar. 28, 2012, the content of which is incorporated herein by reference.

BACKGROUND ART

In recent years, from the viewpoint of environmental load reduction, there has been a need for environmentally friendly and clean liquid fuels with a low sulfur content and aromatic hydrocarbon content. From such a viewpoint, as technology which is able to produce a fuel base stock, specifically kerosene or gas oil base stock, not including a sulfur content or aromatic hydrocarbons, that is rich in aliphatic hydrocarbons, methods utilizing the Fischer-Tropsch synthesis reaction (hereunder referred to as "FT synthesis reaction"), in which carbon monoxide gas (CO) and hydrogen gas ($H_2$) are feedstock gases, are being investigated (refer to Patent Document 1 for example).

Conventionally, as a method for producing hydrocarbon oils by the FT synthesis method, a method has been disclosed using a bubble column slurry bed reactor, in which the FT synthesis reaction is performed by blowing a synthesis gas (a mixed gas with CO and $H_2$ as principal components) into a slurry in which FT synthesis reaction catalyst particles are suspended within the hydrocarbon oil as a liquid medium (refer to Patent Document 2 for example).

In such a bubble column slurry bed reactor, in a case where the FT synthesis reaction activity of the catalyst (FT synthesis reaction catalyst particles) during operation has decreased, it is necessary to perform temperature compensation of this activity decrease by raising the reaction temperature for example. However, if the reaction temperature is increased, there is a problem in that the chain growth probability α and the selectivity toward hydrocarbon oils with 5 carbon atoms or more (hereunder also referred to as $C_5^+$) decreases (refer to Non-Patent Document 1). An FT synthesis reaction having a high synthesis gas conversion rate (carbon monoxide conversion rate) and being able to obtain $C_5^+$ in good yields (high $C_5^+$ selectivity) is desirable from the viewpoint of economic efficiency since the product oil yield increases. Therefore, to continue to make the reaction temperature high in order to maintain the FT synthesis reaction activity of the catalyst results in the $C_5^+$ selectivity decreasing and the product oil yield decreasing, and it is not preferable from the viewpoint of economic efficiency.

Therefore, in a case where the FT synthesis reaction activity of the catalyst during operation has decreased, instead of making the reaction temperature high, it is necessary to fill the reactor with fresh catalyst. As a method of filling the reactor with fresh catalyst in this manner, conventionally, a catalyst filling apparatus and a catalyst filling method by the device disclosed in Patent Document 2 is known for example. The technology of Patent Document 2 is such that the slurry is prepared by suspending only a fresh catalyst within the hydrocarbon oil in the slurry preparation tank provided separately to the reactor, and next, by introducing an inert gas, such as nitrogen, to the slurry preparation tank, and making the pressure inside the slurry preparation tank higher than the pressure of the reactor, pressure transfer of the slurry in the slurry preparation tank to the reactor is performed.

PRIOR ART DOCUMENTS

Patent Documents

Patent Document 1: Japanese Unexamined Patent Application, First Publication No. 2004-323626.
Patent Document 2: U.S. Pat. No. 6,974,844.

Non-Patent Document

Non-Patent Document 1: C. N. Hamelinck et al., Energy 29 (2004), 1743-1771.

DISCLOSURE OF INVENTION

Problems to be Solved by the Invention

However, there are characteristic difficulties in the handling of slurry. That is, since it is necessary for the slurry to maintain a state in which the catalyst is suspended in the hydrocarbon oil, if the mixing and the stirring are stopped, the catalyst eventually settles due to gravity and separates from the hydrocarbon oil for example. Therefore, even when a slurry in which catalyst preparation is finished is charged into the reactor while the catalyst in the reactor is drawn out, the inventor has focused on the settling and the separation of the catalyst from the slurry during the operation, and the blocking of the lines and the valves. In other words, in the charging operation mentioned above, in order to maintain the liquid surface height in the reactor, the draw-out and charging flow rates must be controlled by providing valves on the draw-out line and the charging line, and by adjustment of the valves, such that the draw-out speed and the charging speed become approximately equivalent. Consequently, since the valves are throttled (not fully opened) in order to control the flow rates, the charged slurry passes through a narrow flow path. Furthermore, the flow rates cannot be made very high. As a result, the state of the slurry changes during the charging operation, the catalyst within the slurry begins to settle midway through the charging process time (such as the second half of the entire operation time), and blockage occurs in the middle of the lines and the valves, and the like.

Furthermore, in the technology of Patent Document 2, there is concern that, by performing pressure transfer of the slurry to the reactor, the slurry liquid surface height in the reactor may rapidly change, or as a result of the inert gas introduced to the slurry preparation tank blowing through the reactor when the filling of catalyst in the reactor is completed, the operation conditions such as the temperature or pressure of the reactor may change, or the fluid state of the slurry in the reactor may rapidly fluctuate.

Therefore, in the technology mentioned above, since fresh catalyst cannot be introduced during stationary operation, it is necessary to change the course of the FT synthesis reaction to a significantly inhibited operation condition, or to perform pressure transfer and filling of the slurry into the reactor in a state where the operation is temporarily stopped. Hence mechanical loss, operation time, operation costs and the like, become a problem.

The present invention takes into consideration the aforementioned circumstances, with an object of providing a catalyst filling apparatus of a bubble column slurry bed reactor and a catalyst filling method of a bubble column slurry bed reactor wherein, when the FT synthesis reaction catalyst is filled into the bubble column slurry bed reactor, fresh catalyst can be rapidly filled into the reactor without the catalyst settling and separating, while stably continuing stationary operation and without changing the course of the FT synthesis reaction to a significantly inhibited operation condition or temporarily stopping the operation.

Means for Solving the Problem

As a result of keen examination to solve the aforementioned problem, the present inventor has found out that by providing the slurry preparation tank adjacent to the bubble column slurry bed reactor, and by circulating the slurry by communicating their respective upper parts and lower parts with lines, fresh catalyst can be filled into the reactor while stably continuing stationary operation.

The catalyst filling apparatus of the bubble column slurry bed reactor of the present invention is used for a Fischer-Tropsch synthesis reaction, the catalyst filling apparatus including:

a slurry preparation tank installed adjacent to the reactor, and configured to prepare a slurry from a Fischer-Tropsch synthesis reaction catalyst and a slurry preparation oil;

an upper part communication line configured to direct the slurry in the reactor to the slurry preparation tank;

an upper part communication line on-off valve provided on the upper part communication line;

a lower part communication line configured to direct the slurry in the slurry preparation tank to the reactor;

a lower part communication line on-off valve provided on the lower part communication line;

a pressure equalizing line configured to communicate an upper part void part in the reactor with an upper part void part in the slurry preparation tank and to make the pressures inside the reactor and the slurry preparation tank the same; and a pressure equalizing line on-off valve provided on the pressure equalizing line, wherein the upper part communication line is connected to the reactor in a position that, with respect to the slurry liquid in the reactor during stationary operation, is equal to or higher than a half level of the slurry liquid in a height direction of the reactor and is lower than a liquid surface of the slurry, the upper part communication line is downwardly inclined from the reactor toward the slurry preparation tank, and is connected to the slurry preparation tank in a position that is equal to or higher than a half level of the slurry preparation tank in a height direction of the slurry preparation tank, the lower part communication line is connected to the reactor in a position that, with respect to the slurry liquid in the reactor during stationary operation, is lower than the half level of the slurry liquid in the height direction of the reactor, the lower part communication line is upwardly inclined from the reactor toward the slurry preparation tank, and is connected to the slurry preparation tank in a position that is the lower end section of the slurry preparation tank, and the slurry preparation tank is provided with a catalyst charging device configured to charge a Fischer-Tropsch synthesis reaction catalyst, an inert gas introducing device configured to introduce an inert gas to the slurry preparation tank, a slurry preparation oil supplying device configured to supply a slurry preparation oil, a slurry heating device that heats the slurry in the slurry preparation tank, and a slurry stirring device configured to stir the slurry to mix the slurry.

The catalyst filling method of a bubble column slurry bed reactor of the present invention is a used for a Fischer-Tropsch synthesis reaction by the catalyst filling apparatus of a bubble column slurry bed reactor mentioned above, the catalyst filling method including:

a slurry preparation step of stirring a slurry preparation oil in the slurry preparation tank on heating to make a prepared slurry in which the catalyst is suspended within the slurry preparation oil;

a purging step in which an inert gas is introduced to the slurry preparation tank by the inert gas introducing device to replace oxygen within the prepared slurry and the slurry preparation tank with inert gas;

a pressure equalization step after the purging step, in which the pressure equalizing line on-off valve is opened to make the pressures inside the reactor and the slurry preparation tank the same;

a slurry circulation step after the pressure equalization step, in which the slurry in the slurry preparation tank is introduced to the reactor while introducing the slurry in the reactor to the slurry preparation tank by opening the upper part communication line on-off valve and the lower part communication line on-off valve, and a slurry circulation completion step following the slurry circulation step, in which the upper part communication line on-off valve and the pressure equalizing line on-off valve are closed, subsequently the inert gas is introduced to the slurry preparation tank by the inert gas introducing device to pressure transfer the slurry in the slurry preparation tank via the lower part communication line to the reactor, and thereafter the lower part communication line on-off valve is closed.

Effects of the Invention

According to the catalyst filling apparatus of a bubble column slurry bed reactor and the catalyst filling method of a bubble column slurry bed reactor of the present invention, the slurry preparation tank is installed adjacent to the bubble column slurry bed reactor. Therefore, by communicating the upper part void part in the reactor with the upper part void part in the slurry preparation tank via the pressure equalizing line and making the pressures inside the reactor and the slurry preparation tank the same, along with communicating the upper part of the reactor with the upper part of the slurry preparation tank in that state via the upper part communication line, and communicating the lower part of the reactor with the lower part of the slurry preparation tank via the lower part communication line, the slurry can be circulated between the reactor and the slurry preparation tank by its own weight. Therefore, an exceptional effect can be achieved in which a slurry with fresh catalyst can be rapidly charged into the reactor without the lines blocking as a result of the catalyst within the slurry settling and separating from the slurry preparation oil.

In a state where the slurry is circulated in this manner, when the pressure equalizing line and the upper part communication line are closed and the inert gas is introduced to the slurry preparation tank, the slurry in the slurry preparation tank can be completely pressure-transferred from the lower part communication line to the reactor. At that time, since the slurry containing fresh catalyst in the slurry preparation tank is already transported to the reactor and circulated therein, stationary operation is performed in the reactor. Therefore, the inert gas is gradually introduced to the slurry preparation tank at a flow rate that is the necessary minimum, and the slurry remaining in the slurry preparation tank can be gradually pressure-transferred to the reactor. As a result, inconveniences such as the inert gas introduced to the slurry preparation tank blowing through the reactor and changing the operation conditions, such as the temperature and the pressure of the reactor, or rapidly changing the fluid state of the slurry, can be prevented.

Therefore, with the present invention, with respect to the operation of the bubble column slurry bed reactor, fresh catalyst can be filled into the reactor while stably continuing stationary operation without changing the course of the FT synthesis reaction to a significantly inhibited operation condition, or temporarily stopping the operation. Furthermore, since fresh catalyst can be introduced during stationary operation, an exceptional effect can be achieved in which losses in mechanical loss, operation time, operation costs, and the like, can be avoided.

BEST MODE FOR CARRYING OUT THE INVENTION

Hereunder, a catalyst filling apparatus of a bubble column slurry bed reactor, and a catalyst filling method of a bubble column slurry bed reactor of the present invention are described in detail.

Firstly, a liquid fuel synthesis system containing a bubble column slurry bed reactor according to the present invention is described with reference to FIG. 1.

Figure 1:
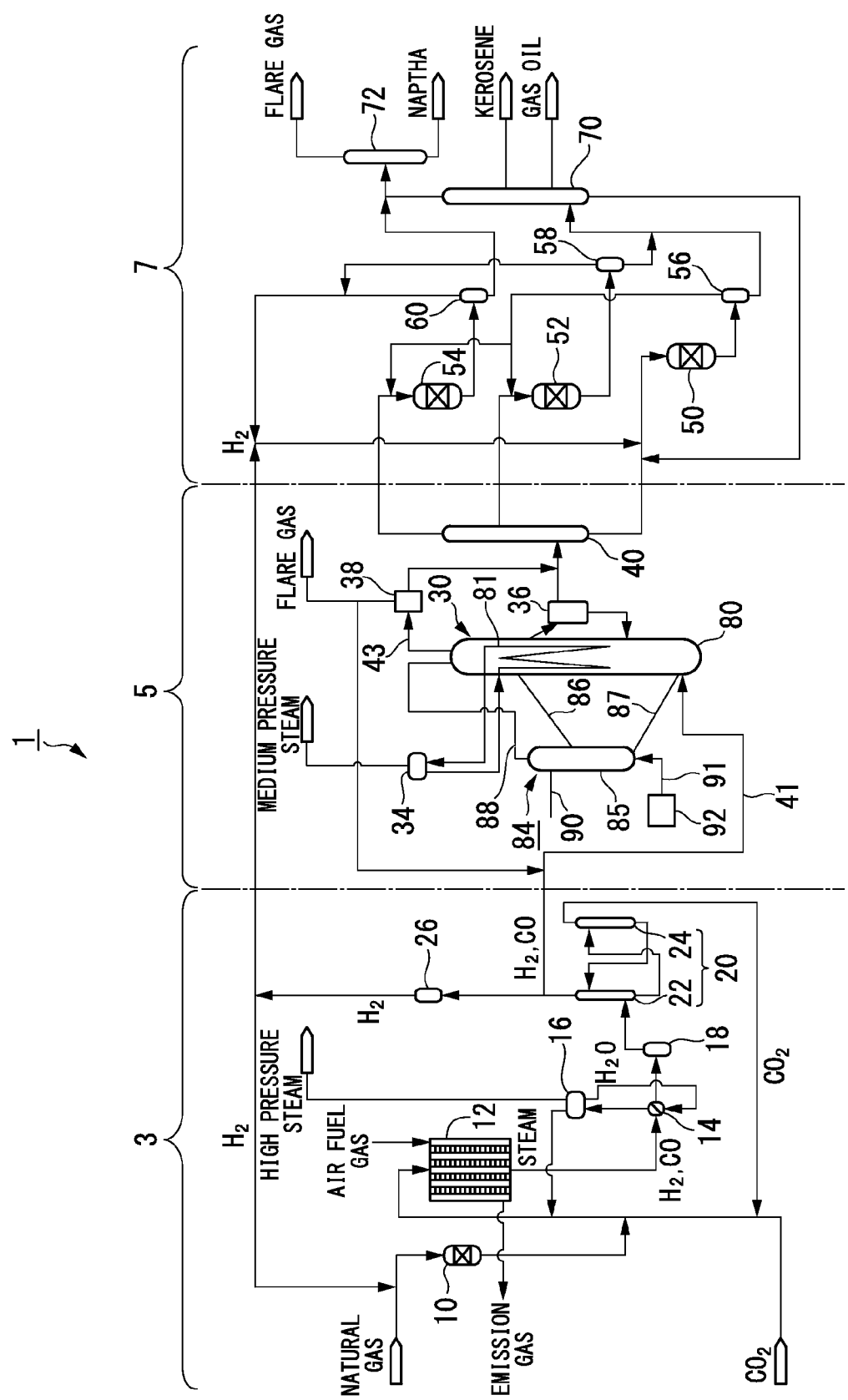
FIG. 1 is a schematic diagram showing an example of the overall configuration of a liquid fuel synthesis system according to the present invention.

The liquid fuel synthesis system 1 shown in FIG. 1 is a plant that executes GTL processes which convert hydrocarbon feedstocks, such as natural gas, into liquid fuels.

The liquid fuel synthesis system 1 is configured by a synthesis gas production unit 3, a FT synthesis unit 5, and an upgrading unit 7. The synthesis gas production unit 3 reforms natural gas, which is the hydrocarbon feedstock, and produces synthesis gas containing carbon monoxide gas and hydrogen gas. The FT synthesis unit 5 synthesizes liquid hydrocarbons from the synthesis gas produced in the synthesis gas production unit 3, by the FT synthesis reaction. The upgrading unit 7 produces the base stock of the liquid fuel (primarily kerosene and gas oil) by hydrogenating and purifying the liquid hydrocarbons synthesized by the FT synthesis reaction.

Hereunder, the configuration elements of the respective units are described.

The synthesis gas production unit 3 is primarily furnished with, for example, a desulfurization reactor 10, a reformer 12, a waste heat boiler 14, vapor-liquid separators 16 and 18, a $CO_2$ removal unit 20, and a hydrogen separator 26. The desulfurization reactor 10 is configured by a hydrogenation desulfurizer and the like, and removes sulfur compounds from natural gas, which is the feedstock. The reformer 12 reforms the natural gas supplied from the desulfurization reactor 10, and generates synthesis gas containing carbon monoxide gas (CO) and hydrogen gas ($H_2$) as the primary components. The waste heat boiler 14 recovers the waste heat of the synthesis gas generated at the reformer 12, and generates high-pressure steam.

The vapor-liquid separator 16 separates the water heated in the waste heat boiler 14 by heat-exchanging with the synthesis gas, into a vapor (high-pressure steam) and a liquid. The vapor-liquid separator 18 removes the condensate component from the synthesis gas cooled in the waste heat boiler 14, and supplies the gas component to the $CO_2$ removal unit 20. The $CO_2$ removal unit 20 has an absorption tower 22 that removes carbon dioxide gas from the synthesis gas supplied from the vapor-liquid separator 18 using an absorbent, and a regeneration tower 24 that performs regeneration by stripping the carbon dioxide gas from the absorbent containing the carbon dioxide gas. The hydrogen separator 26 separates from the synthesis gas, from which the carbon dioxide gas has been separated by the $CO_2$ removal unit 20, a portion of the hydrogen gas contained in the synthesis gas. However, there are also cases where it is not necessary to provide the $CO_2$ removal unit 20, depending on circumstances.

Among these, the reformer 12 reforms natural gas using carbon dioxide gas and steam by the steam and carbon dioxide gas reforming method represented by the chemical reaction formulas (1) and (2) mentioned below for example, and generates a high-temperature synthesis gas with carbon monoxide gas and hydrogen gas as the primary components. This reforming method of the reformer 12 is in no way limited to the example of the steam and carbon dioxide gas reforming method mentioned above, and the steam reforming method, the partial oxidation reforming method (PDX), which uses oxygen, the autothermal reforming method (ATR), which is a combination of the partial oxidation reforming method and the steam reforming method, and the carbon dioxide gas reforming method can also be utilized for example.

$$CH_4+H_2O \rightarrow CO+3H_2 \quad (1)$$

$$CH_4+CO_2 \rightarrow 2CO+2H_2 \quad (2)$$

Furthermore, the hydrogen separator 26 is provided on a branch line that branches from the main line connecting the $CO_2$ removal unit 20 or the vapor-liquid separator 18 and the bubble column slurry bed reactor 30.

The hydrogen separator 26 can be configured by a hydrogen PSA (Pressure Swing Adsorption) device that performs the adsorption and the desorption of hydrogen by utilizing pressure differentials for example. This hydrogen PSA device has an adsorbent material (a zeolite-type adsorbent material, activated carbon, alumina, silica gel, and the like) within a plurality of adsorption towers (not shown in the drawing) arranged in parallel. By sequentially repeating the steps of pressurization, adsorption, desorption (depressurization) and purging of hydrogen at the respective adsorption towers, high-purity hydrogen gas (approximately 99.999% for example) separated from the synthesis gas can be continuously supplied to the various hydrogen-utilizing reactors (the desulfurization reactor 10, the wax fraction hydrocracking reactor 50, the middle distillate hydrotreating reactor 52, and the naphtha fraction hydrotreating reactor 54 for example) that perform predetermined reactions by utilizing hydrogen.

The hydrogen gas separation method of the hydrogen separator 26 is in no way limited to the example of the pressure swing adsorption method such as the hydrogen PSA device mentioned above, and it may be the hydrogen absorbing alloy adsorption method, the membrane separation method, or a combination of these for example.

Next, the FT synthesis unit 5 is described. As shown in FIG. 1, the FT synthesis unit 5 is primarily provided with a bubble column slurry bed reactor 30, a vapor-liquid separator 34, a catalyst separator 36, a vapor-liquid separator 38, and a first fractionator 40.

The bubble column slurry bed reactor (hereunder, also simply referred to as "reactor") 30 is one that synthesizes liquid hydrocarbons from the synthesis gas provided by the supply line 41 connected to the synthesis gas production unit 3, and functions as a reactor for FT synthesis that synthesizes liquid hydrocarbons from synthesis gas by the FT synthesis reaction.

Figure 2:
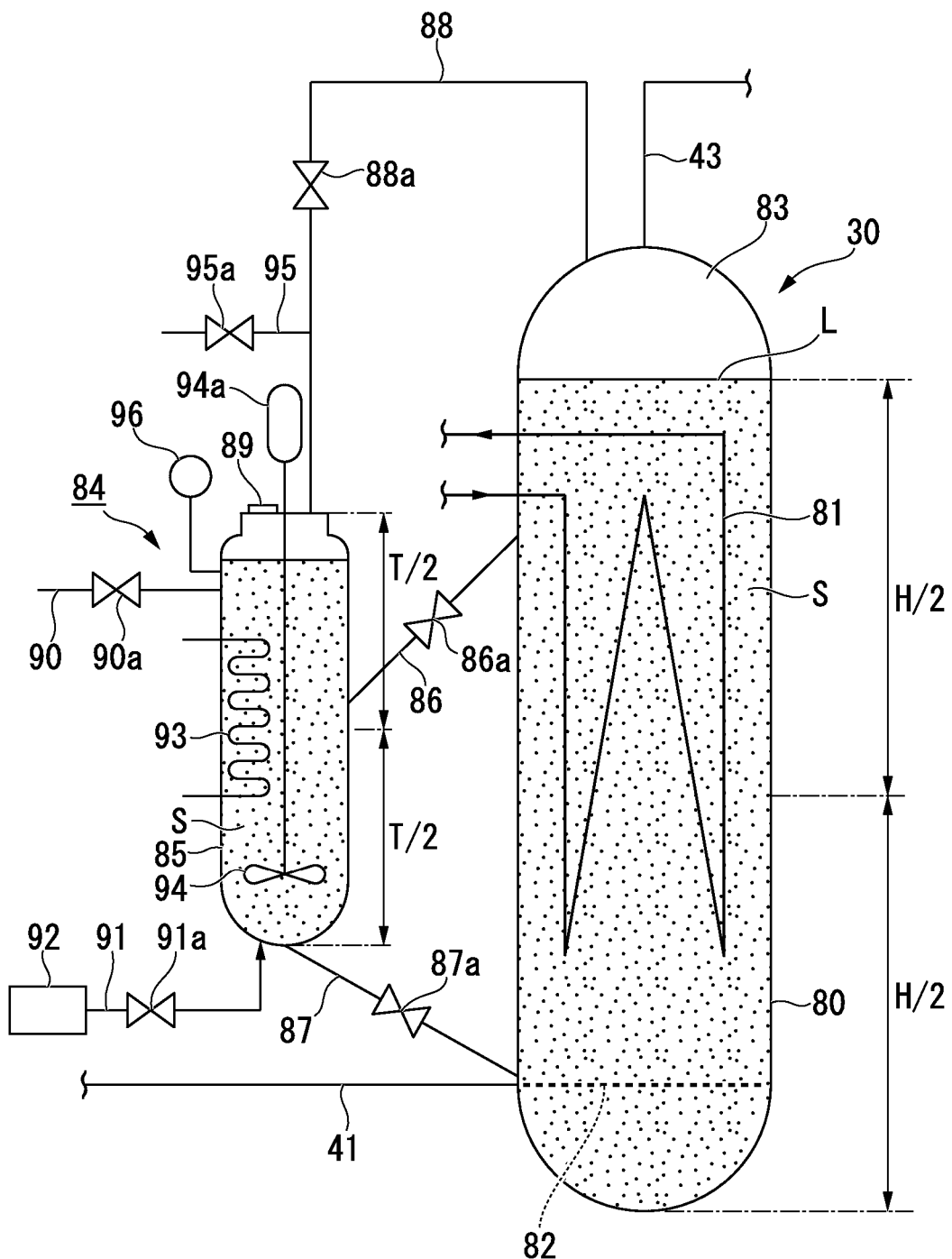
FIG. 2 is a schematic block diagram of an FT synthesis unit according to the present invention.

As shown in FIG. 2, the reactor 30 is primarily provided with a reactor body 80 and cooling lines (heat removal lines) 81, and is driven under conditions in which the interior of the reactor 30 is maintained at approximately 190 to 270° C. for example, and pressurized above atmospheric pressure. The reactor body 80 is an approximate cylindrical type metallic vessel. A slurry in which solid catalyst particles, that is, FT synthesis reaction catalyst particles, are suspended within the liquid hydrocarbon (product of the FT synthesis reaction), is housed within the reactor body 80, and a slurry floor is formed by the slurry.

A sparger 82 is arranged on the lower part of this reactor body 80, and by the sparger 82, the synthesis gas having hydrogen gas and carbon monoxide gas as the primary components is injected into the slurry S. The synthesis gas blown into the slurry S becomes bubbles and rises upward within the slurry in the reactor body 80 in a height direction (vertical direction) of the reactor body 80. In the process thereof, the synthesis gas is dissolved within the liquid hydrocarbons, and by coming into contact with the catalyst particles, the synthesis reaction (FT synthesis reaction) of the liquid hydrocarbons proceeds. Specifically, the hydrocarbons are generated by hydrogen gas and carbon monoxide gas reacting in the manner shown in the chemical reaction formula (3) below.

$$2nH_2 + nCO \rightarrow (-CH_2-)_n + nH_2O \quad (3)$$

Here, in a reaction of this manner, the proportion of carbon monoxide gas consumed in the reactor 30 with respect to the carbon monoxide gas (CO) supplied to the reactor 30 is made the carbon monoxide conversion rate (hereunder, also simply referred to as "conversion rate") of the FT synthesis reaction. This conversion rate is calculated as a percentage from the molar flow rate of carbon monoxide gas within the gas flowing into the reactor body 80 per unit time (inlet CO molar flow rate) and the molar flow rate of carbon monoxide gas within the gaseous discharged component drawn out from the gas phase part 83 of the reactor body 80 per unit time as mentioned below (outlet CO molar flow rate). That is, the conversion rate is evaluated according to the formula (4) below.

$$\text{Conversion rate} = \frac{\text{Inlet CO molar flow rate} - \text{outlet CO molar flow rate}}{\text{Inlet CO molar flow rate}} \times 100 \quad (4)$$

In order to recycle the synthesis gas that was unreacted in the reactor body 80 and contained in the gaseous discharged component that is discharged from the gas phase part 83 of the reactor 30, what is normally performed is for the gaseous discharged component to be cooled, and for the gas component separated from the condensed liquid component to be recycled to the reactor 30 and provided again for reaction. In that case, the inlet CO molar flow rate refers to the molar flow rate of carbon monoxide gas within the reactor inlet gas, which consists of newly supplied synthesis gas and the recycled gas.

The molar flow rate of carbon monoxide gas within the synthesis gas flowing into the reactor body 80 per unit time (inlet CO molar flow rate) is continuously or periodically measured by a gas chromatography device and a flow meter (not shown in the drawing) provided on the supply line 41 that supplies the synthesis gas to the reactor body 80 for example. As mentioned above, in a case where gas containing unreacted synthesis gas is recycled to the reactor body 80, the position in which the gas chromatography device and the flow meter are installed on the supply line 41 may be further downstream than the junction with the line in which the recycled gas flows.

Furthermore, the molar flow rate of carbon monoxide gas within the discharged component that is drawn out from the gas phase part 83 of the reactor body 80 per unit time (outlet CO molar flow rate) is continuously or periodically measured by the gas chromatography device and a flow meter (not shown in the drawing) provided on the gas line downstream of the vapor-liquid separator 38 (refer to FIG. 1). Therefore, from such measured values, the conversion rate of carbon monoxide is continuously or periodically calculated based on the formula (4), and the operation of the reactor 30 is monitored by this result.

Furthermore, as a result of the synthesis gas rising in the reactor body 80 as bubbles, an upward flow (air lift) of the slurry S is generated in the reactor body 80. That is, the slurry S repeatedly flows from the lower part to the upper part of the reactor 30 at the central part (in the vicinity of the center) of the reactor 30, and flows from the upper part to the lower part of the reactor 30 at the outside part (in the vicinity of the outside) of the reactor 30. As a result of this, a circulating flow of the slurry S is generated in the reactor body 80.

The gas phase part 83 is located above the slurry S housed in the reactor body 80. The gas-liquid separation is performed at a liquid surface L of the slurry S (interface between the gas phase part 83 and the slurry S). That is, the synthesis gas that passed through the interface between the slurry S and the gas phase part 83 without reacting within the slurry S, and the comparatively light hydrocarbon generated by the FT synthesis reaction, which is a gaseous state under the conditions in the reactor body 80, are transferred to the gas phase part 83 as a gaseous component. At this time, the liquid droplets accompanying this gaseous component, and the catalyst particles accompanying these liquid droplets are returned to the slurry S by gravity. Further, the gaseous component (the unreacted synthesis gas and the light hydrocarbon) that has risen to the gas phase part 83 of the reactor body 80 is drawn out via the delivery line 43 (line) connected to the gas phase part 83 (upper part) of the reactor body 80, and becomes a gaseous discharged component. The gaseous discharged component is, as mentioned below, supplied to the vapor-liquid separator 38 upon being cooled.

The cooling lines 81 are provided in the reactor body 80, and by removing the reaction heat of the FT synthesis reaction, maintain the temperature within the system at a predetermined temperature. These cooling lines 81 may be such that for example a single line is bent and formed such that it vertically turns back and forth a plurality of times along the vertical direction. Furthermore, for example a plurality of cooling lines of a double line structure referred to as a bayonet-type may be arranged in the reactor body 80. That is, the shape of the cooling lines 81 and the number of lines is in no way limited to the shape and the number of lines mentioned above, and it is acceptable if they are arranged in the reactor body 80 and are able to contribute to the cooling of the slurry.

Cooling water (water in which the difference with the temperature in the reactor body 80 is approximately −50 to 0° C. for example) supplied from the vapor-liquid separator 34 shown in FIG. 1 flows through the cooling lines 81. In the process of the cooling water flowing through the cooling lines 81, the slurry S in the reactor body 80 is cooled by heat-exchanging between the cooling water and the slurry S via the line walls of the cooling lines 81. A portion of the cooling water evaporates and is discharged to the vapor-liquid separator 34, and thereafter is recovered as medium-pressure steam.

The medium for cooling the slurry S in the reactor body 80 is in no way limited to cooling water of the manner mentioned above, and $C_4$ to $C_{10}$ linear, branched and cyclic alkanes, olefins, low-molecular-weight silanes, silylethers, and silicone oil can be utilized for example.

The vapor-liquid separator 34 separates the water that is heated by flowing in the cooling lines 81 arranged in the reactor body 80 as mentioned above, into water vapor (medium-pressure steam) and a liquid. The liquid separated at this vapor-liquid separator 34 is, as mentioned above, supplied to the cooling lines 81 again as cooling water.

There are no particular limitations on the catalyst that constitutes the slurry S housed in the reactor body 80, that is, the FT synthesis reaction catalyst, although a solid particulate catalyst in which at least one type of active metal selected from cobalt, ruthenium, iron, and the like, is supported on a support body composed of an inorganic oxide, such as silica or alumina, is preferably utilized. The catalyst may, in addition to the active metal, have a metal component, such as zirconium, titanium, hafnium, rhenium, and the like, that is added with an object of increasing the activity of the catalyst for example. There are no particular limitations on the shape of this catalyst, although from the viewpoint of the flowability of the slurry S, and from the viewpoint of inhibiting the generation of pulverized catalyst particles when it is flowed, resulting from the disintegration or the abrasion of the catalyst particles as a result of collisions or friction of the catalyst particles with each other, and the catalyst particles with the inner wall of the reactor body 80, the cooling line 81, and the like, it is preferable for it to be an approximately spherical shape.

Furthermore, there are no particular limitations on the average particle size of the catalyst particles, although from the viewpoint of the flowability of the slurry S, it is preferable for it to be approximately 40 to 150 μm.

The catalyst separator 36 separates the slurry S into a solid component of the catalyst particles and the like, and a liquid component containing the liquid hydrocarbons. For the separated solid component of the catalyst particles and the like, a portion thereof is returned to the reactor body 80, and the liquid component is supplied to the first fractionator 40.

Furthermore, a gas phase part 83 is provided as mentioned above on the upper part (tower top part) of the reactor body 80, and the delivery line 43 is connected to the tower top of the reactor body 80.

The delivery line 43 is connected to the vapor-liquid separator 38, and transports the gaseous component (gaseous discharged component) within the gas phase part 83 that has risen to the tower top of the reactor body 80, to the vapor-liquid separator device 38. The gaseous component is a FT gas component containing unreacted synthesis gas (feedstock gas) and a synthesized hydrocarbon gas component.

The vapor-liquid separator 38 cools the FT gas component by a heat exchanger (not shown in the drawing), separates a portion of the liquid hydrocarbons (light FT hydrocarbons) of the condensate, and introduces it to the first fractionator 40. On the other hand, the gas component separated at the vapor-liquid separator 38 has unreacted synthesis gas (CO and $H_2$) and hydrocarbons with two or less carbon atoms as the primary components, and a portion is charged again into the bottom part of the reactor body 80 (reactor 30) and recycled to the FT synthesis reaction. Furthermore, the gas component that is not recycled to the FT synthesis reaction is discharged to the off-gas side, and is utilized as a fuel gas, or the fuel corresponding to LPG (liquid petroleum gas) is recovered, or it is recycled as a feedstock of the reformer 12 of the synthesis gas production unit 3.

As shown in FIG. 2, the bubble column slurry bed reactor 30 is provided with a catalyst filling apparatus 84 for filling fresh catalyst into the reactor 30. The catalyst filling apparatus 84 is an embodiment of the catalyst filling apparatus of a bubble column slurry bed reactor of the present invention, and is furnished with a slurry preparation tank 85 installed adjacent to the reactor 30. The slurry preparation tank 85 is configured to make a prepared slurry from fresh FT synthesis reaction catalyst (hereunder also simply referred to as "catalyst") and hydrocarbon oil (slurry preparation oil), and supplies the prepared slurry to the reactor 30.

An upper part communication line 86, a lower part communication line 87, and a pressure equalizing line 88 are connected to the slurry preparation tank 85. Moreover, the upper part communication line 86, the lower part communication line 87, and the pressure equalizing line 88 are also connected to the reactor 30 (reactor body 80). Therefore, the reactor 30 is mutually communicated with the slurry preparation tank 85 via the upper part communication line 86, the lower part communication line 87, and the pressure equalizing line 88. During stationary operation, the reactor 30 is isolated from the slurry preparation tank 85 by closing on-off valves mentioned below.

The upper part communication line 86 serves to direct the slurry S from the reactor 30 to the slurry preparation tank 85, and is arranged downwardly inclined from the reactor 30 toward the slurry preparation tank 85. For example, the upper part communication line 86 is arranged between the reactor 30 and the slurry preparation tank 85 so as to be inclined at approximately 45 degrees. By being arranged at such an inclination angle, when the slurry flows within the upper part communication line 86 in a manner mentioned below, the catalyst particles do not settle and remain on an inner surface of the line, but flow down along the incline.

Furthermore, in order to simplify the arrangement of the upper part communication line 86 at such an angle, and to increase the degree of freedom of the installation position of the slurry preparation tank 85 with respect to the reactor 30, the connection position of the upper part communication line 86 with respect to the reactor 30 is, with respect to the slurry S in the reactor 30 during stationary operation, equal to or higher than a half level of the slurry S in the height direction of the reactor 30 and is lower than the liquid surface L of the slurry S. On the other hand, the connection position of the upper part communication line 86 with respect to the slurry preparation tank 85 is equal to or higher than a half level of the slurry preparation tank 85 in the height direction of the slurry preparation tank 85. Where the height dimension of the slurry S in the reactor 30 is assumed as "H", and that of the slurry preparation tank 85 is "T".

The lower part communication line 87 serves to direct the slurry S in the slurry preparation tank 85 from the slurry preparation tank 85 to the reactor 30, and is arranged downwardly inclined from the slurry preparation tank 85 toward the reactor 30. That is, it is arranged upwardly inclined from the reactor 30 toward the slurry preparation tank 85. For example, the lower part communication line 87 is arranged between the reactor 30 and the slurry preparation tank 85 so as to be inclined at approximately 45 degrees. By being arranged at such an inclination angle, when the slurry flows within the lower part communication line 87, the catalyst particles do not settle and remain on an inner surface of the line, but flow down along the incline.

In order to simplify the arrangement of the lower part communication line 87 at such an angle, and to increase the degree of freedom of the installation position of the slurry preparation tank 85 with respect to reactor 30, the connection position of the lower part communication line 87 with respect to the reactor 30 is, with respect to the slurry S in the reactor 30 during stationary operation, lower than the half level of the slurry S in the height direction of the reactor 30. On the other hand, the connection position of the lower part communication line 87 with respect to the slurry preparation tank 85 is the lower end section of the slurry preparation tank 85.

The pressure equalizing line 88 serves to make the pressure inside the reactor 30 and the pressure inside the slurry preparation tank 85 the same pressure, and is arranged between the upper part (tower top part) of the reactor 30 and the upper part (tower top part) of the slurry preparation tank 85. Consequently, the pressure equalizing line 88 communicates the upper part void part in the reactor 30 (that is the gas phase part 83) with the upper part void part in the slurry preparation tank 85, and adjusts the pressures inside the reactor 30 and the slurry preparation tank 85 to the same. On the pressure equalizing line 88, a vent line 95 is located closer to the slurry preparation tank 85 than a pressure equalizing line on-off valve 88a. A vent valve 95a is provided on the vent line 95, and the downstream side of the vent valve 95a is open to the atmosphere via a flaring system and the like.

Furthermore, the upper part communication line 86, the lower part communication line 87 and the pressure equalizing line 88 are provided with on-off valves available to open and close the lines. The upper part communication line 86 is provided with an upper part communication line on-off valve 86a, the lower part communication line 87 is provided with a lower part communication line on-off valve 87a, and the pressure equalizing line 88 is provided with the pressure equalizing line on-off valve 88a. By operating the on-off valves 86a, 87a, and 88a, the reactor 30 is maintained to communicate with the slurry preparation tank 85 via the upper part communication line 86, the lower part communication line 87 and the pressure equalizing line 88, or is isolated from the slurry preparation tank 85 and closed.

Moreover, the slurry preparation tank 85 is provided on the uppermost part thereof with a catalyst charging inlet 89 for charging the FT synthesis reaction catalyst, and a hopper (not shown in the drawing) for supplying the catalyst is connected to the catalyst charging inlet 89. Based on such a configuration, fresh catalyst is able to be charged into the slurry preparation tank 85 from the catalyst charging inlet 89. Here, the catalyst charging device of the present invention is formed by the catalyst charging inlet 89 and a catalyst supplying device, such as a hopper.

A slurry preparation oil supply line 90 that supplies the slurry preparation oil to the preparation tank 85 is connected to the upper part of the slurry preparation tank 85. An on-off valve 90a is provided on the slurry preparation oil supply line 90, and furthermore, a storage tank (not shown in the drawing) that stores the slurry preparation oil and a pump (not shown in the drawing) that pressure transfers the slurry preparation oil in the storage tank are provided. The slurry preparation oil supplying device of the present invention is configured by the storage tank, the pump, the slurry preparation oil supply line 90, and the on-off valve 90a. Further, by the slurry preparation oil supplying device, by pressure transferring the slurry preparation oil in the storage tank with the pump, the slurry preparation oil can be supplied via the slurry preparation oil supply line 90 to the slurry preparation tank 85. As the slurry preparation oil, a hydrocarbon oil having wax as the primary component is used for example.

Furthermore, an inert gas introduction line 91 that introduces inert gas, such as nitrogen, to the slurry preparation tank 85, is connected to the bottom part (lower part) of the slurry preparation tank 85. An on-off valve 91a is provided on the inert gas introduction line 91, and furthermore, an inert gas source 92, such as a high-pressure nitrogen source, is provided. The inert gas introducing device of the present invention is configured by the inert gas source 92, the inert gas introduction line 91, and the on-off valve 91a. Further, by the slurry preparation oil supplying device, the inert gas supplied from the inert gas source 92 can be introduced to the slurry preparation tank 85 from the bottom part thereof via the inert gas introduction line 91.

Moreover, a heating tube (slurry heating device) 93 is installed in the slurry preparation tank 85. A heating medium such as a hydrocarbon oil is flowed through the heating tube 93. The heating tube 93 serves to heat the slurry in the slurry preparation tank 85 to a predetermined temperature, for example a temperature sufficiently higher than the melting point of the slurry preparation oil.

A stirrer (slurry stirring device) 94 is installed in the slurry preparation tank 85. The stirrer 94 is rotated by a motor 94a arranged outside the slurry preparation tank 85, and serves to uniformly stir and mix the slurry in the slurry preparation tank 85.

Furthermore, the slurry preparation tank 85 is provided with a liquid surface measurement device 96 configured to measure the level of the slurry (liquid surface level of the slurry) that has been filled.

The first fractionator 40 shown in FIG. 1 fractionally distills the liquid hydrocarbons supplied from the bubble column slurry bed reactor 30 via the catalyst separator 36 and the vapor-liquid separator 38, and fractionally distills into a naphtha fraction (boiling point lower than approximately 150° C.), a middle distillate corresponding to kerosene and gas oil (boiling point of approximately 150 to 360° C.), and a wax component (boiling point exceeding approximately 360° C.). The wax component fractionally distilled here can be used as a portion of the slurry preparation oil.

The liquid hydrocarbons of the wax component (primarily $C_{21}$ and above) taken out from the bottom part of the first fractionator 40 are transported to the wax fraction hydrocracking reactor 50 of the upgrading unit 7 shown in FIG. 1. Furthermore, the liquid hydrocarbons of the middle distillate (primarily $C_{11}$ to $C_{20}$) taken out from the middle part of the first fractionator 40 are transported to the middle distillate hydrotreating reactor 52 of the upgrading unit 7. Moreover, the liquid hydrocarbons of the naphtha fraction (primarily $C_5$ to $C_{10}$) taken out from the upper part of the first fractionator 40 are transported to the naphtha fraction hydrotreating reactor 54 of the upgrading unit 7.

The upgrading unit 7 is provided with the wax fraction hydrocracking reactor 50, the middle distillate hydrotreating reactor 52, the naphtha fraction hydrotreating reactor 54, vapor-liquid separators 56, 58, and 60, a second fractionator 70, and a naphtha stabilizer 72. The wax fraction hydrocracking reactor 50 is connected to the tower bottom of the first fractionator 40. The middle distillate hydrotreating reactor 52 is connected to the middle part of the first fractionator 40. The naphtha fraction hydrotreating reactor 54 is connected to the upper part of the first fractionator 40. The vapor-liquid separators 56, 58, and 60 are provided respectively corresponding to the hydrogenation reactors 50, 52, and 54. The second fractionator 70 fractionally distills the liquid hydrocarbons supplied from the vapor-liquid separators 56 and 58 according to their boiling points. The naphtha stabilizer 72 fractionates the liquid hydrocarbons of the naphtha fraction supplied from the vapor-liquid separator 60 and the second fractionator 70, wherein the gaseous component of $C_4$ and below is recovered as a fuel gas or discharged as a flare gas, and the component with five or more carbon atoms is recovered as naphtha as a finished product.

Next, the step by which liquid fuel is synthesized from natural gas (GTL process) by the liquid fuel synthesis system 1 of the configuration mentioned above is described.

The liquid fuel synthesis system 1 is supplied with natural gas (primary component of $CH_4$) as a hydrocarbon feedstock from an external natural gas supply source (not shown in the drawing) such as a natural gas field or a natural gas plant. The synthesis gas production unit 3 reforms this natural gas, and produces synthesis gas (a mixed gas having carbon monoxide gas and hydrogen gas as the primary components).

Firstly, the natural gas is supplied, together with the hydrogen gas separated by the hydrogen separator 26, to the desulfurization reactor 10. The desulfurization reactor 10 uses hydrogen gas and hydrogenates the sulfur compounds contained in the natural gas with a known hydrodesulfurization catalyst to convert to hydrogen sulfide. Furthermore, it performs the desulfurization of the natural gas by adsorbing and removing this hydrogen sulfide by an adsorbent material such as zinc oxide. By desulfurizing the gas beforehand in such a manner, the reduction in the activity of the catalyst used in the reformer 12 and the bubble column slurry bed reactor 30, the upgrading unit 7, and the like as a result of sulfur compounds can be prevented.

The natural gas desulfurized in this manner (may contain carbon dioxide gas) is supplied to the reformer 12 following mixing of carbon dioxide gas ($CO_2$) supplied from a carbon dioxide gas supply source (not shown in the drawing) with water vapor generated at the waste heat boiler 14. The reformer 12, by the steam and carbon dioxide gas reforming method, reforms the natural gas using carbon dioxide gas and steam, and a high-temperature synthesis gas having carbon monoxide gas and hydrogen gas as the primary components is generated for example. At this time, the reformer 12 is supplied for example with natural gas and air for the burner provided in the reformer 12, and by the combustion heat of the natural gas in the burner and the radiant heat in the furnace of the reformer 12, the reaction heat necessary for the steam and carbon dioxide gas reforming reaction, which is an endothermic reaction, is provided.

In this manner, the high-temperature synthesis gas (900° C., 2.0 MPaG for example) produced in the reformer 12 is supplied to the waste heat boiler 14, and by heat exchange with the water flowing through the waste heat boiler 14, it is cooled (to 400° C. for example), and waste heat is recovered. At this time, in the waste heat boiler 14, the water heated by the synthesis gas is supplied to the vapor-liquid separator 16, the gaseous component is supplied from this vapor-liquid separator 16 to the reformer 12 or other external devices as high-pressure steam (3.4 to 10.0 MPaG for example), and water of the liquid component is returned to the waste heat boiler 14.

On the other hand, the synthesis gas cooled in the waste heat boiler 14 is supplied to the absorption tower 22 of the $CO_2$ removal unit 20 or the bubble column slurry bed reactor 30 following separation and removal of the condensate liquid component in the vapor-liquid separator 18. The absorption tower 22, by absorbing the carbon dioxide gas contained in the synthesis gas within the stored absorbent, separates the carbon dioxide gas from the synthesis gas. This absorbent containing carbon dioxide gas in the absorption tower 22 is introduced to the regeneration tower 24, and the absorbent containing carbon dioxide gas is heated by steam and a stripping process is performed for example, and the stripped carbon dioxide gas is sent from the regeneration tower 24 to the reformer 12 and recycled to the reforming reaction.

In such a manner, the synthesis gas generated by the synthesis gas production unit 3 is supplied to the bubble column slurry bed reactor 30 of the FT synthesis unit 5. At this time, the composition ratio of the synthesis gas supplied to the bubble column slurry bed reactor 30 is adjusted to a composition ratio ($H_2:CO=2:1$ (molar ratio)) for example) that is suitable for the FT synthesis reaction.

Furthermore, a portion of the synthesis gas, which has had carbon dioxide gas separated by the $CO_2$ removal unit 20, is also supplied to the hydrogen separator 26. The hydrogen separator 26 separates the hydrogen gas contained in the synthesis gas by adsorption and desorption utilizing pressure differentials (hydrogen PSA). The separated hydrogen gas is continuously supplied from a gas holder (not shown in the drawing) via a compressor (not shown in the drawing) to various hydrogen-utilizing reactors (the desulfurization reactor 10, the wax fraction hydrocracking reactor 50, the middle distillate hydrotreating reactor 52, and the naphtha fraction hydrotreating reactor 54 for example) that perform predetermined reactions within the liquid fuel synthesis system 1 by utilizing hydrogen.

Next, the FT synthesis unit 5 synthesizes hydrocarbons from the synthesis gas produced by the synthesis gas production unit 3 by the FT synthesis reaction. That is, the synthesis gas produced by the synthesis gas production unit 3 is supplied to the bubble column slurry bed reactor 30, and provided to the FT synthesis reaction.

The synthesis gas generated by the synthesis gas production unit 3 is flowed in from the bottom part of the bubble column slurry bed reactor 30 via the sparger 82, and becomes bubbles and rises within the slurry housed in the bubble column slurry bed reactor 30. At that time, in the reactor 30, by the FT synthesis reaction mentioned above, the carbon monoxide and the hydrogen gas contained in the synthesis gas react, and hydrocarbon compounds are generated.

The liquid hydrocarbons synthesized in the reactor 30 are introduced as a slurry together with the catalyst particles to the catalyst separator 36.

Here, during stationary operation of the bubble column slurry bed reactor 30, in a case where for example the carbon monoxide conversion rate of the FT synthesis reaction decreases below a set value, and consequently, it is determined that the FT synthesis reaction activity of the FT synthesis reaction catalyst within the slurry S has decreased, in the present invention, fresh FT synthesis reaction catalyst is filled into the bubble column slurry bed reactor 30 by the catalyst filling apparatus 84 shown in FIG. 2 without increasing the reaction temperature and while continuing stationary operation. Hereunder, based on the catalyst filling method to the reactor 30 by the catalyst filling apparatus 84, an embodiment of the catalyst filling method of the present invention is described.

As preparation for slurry preparation, firstly, the on-off valves 86*a*, 87*a*, and 88*a* of the upper part communication line 86, the lower part communication line 87, and the pressure equalizing line 88 are respectively closed, and the communication between the slurry preparation tank 85 in which the slurry has not been filled, and the reactor 30 is closed. The reactor 30 is assumed to be under stationary operation. Further, the vent valve 95*a* is opened in this state, and the inert gas, such as nitrogen, is introduced from the inert gas source 92 to the slurry preparation tank 85. Consequently, the oxygen in the slurry preparation tank 85 and within the systems communicated with this is purged and replaced with the inert gas (purging step). Furthermore, concurrently to, or before and after, this substitution process, the inside of the slurry preparation tank 85 is heated to a predetermined temperature (temperature of the melting point of the slurry preparation oil or higher, approximately 110° C. or higher for example) by the heating tube 93.

Next, the slurry is prepared in the slurry preparation tank 85 (slurry preparation step). That is, a predetermined amount of a hydrocarbon oil, such as wax, is supplied as the slurry preparation oil from the slurry preparation oil supply line 90 to the slurry preparation tank 85. Further, the stirrer 94 is operated and the slurry preparation tank 85 is stirred, and in that state, a predetermined amount of fresh catalyst stored in a hopper, or the like, is charged from the catalyst charging inlet 89 into the slurry preparation tank 85. Consequently, a slurry S achieved by suspending the fresh catalyst within the slurry preparation oil and by uniform mixing is prepared (slurry preparation step). In the meantime, the introduction of the inert gas is continued, and consequently, for example the oxygen (air) mixed in with the supplied catalyst, is replaced with the inert gas, and the oxygen is purged (purging step).

In terms of the amount of slurry that is prepared in this manner, the liquid surface of the slurry is measured by the liquid surface measurement device 96, and it is prepared such that it becomes a preset liquid surface height. At that time, the amount of the slurry is adjusted such that, in the slurry preparation tank 85, a predetermined void (upper part void) is formed in the upper part thereof. Once the catalyst is charged, the catalyst charging inlet 89 is closed airtight by a lid (not shown in the drawing) or the like. Furthermore, once the slurry preparation oil is supplied, the on-off valve 90 of the slurry preparation oil supply line 90 is also closed.

Further, in addition to stopping the introduction of inert gas by closing the on-off valve 91 of the inert gas introduction line 91, the vent valve 95*a* is also closed. Consequently, following purging of the oxygen in the slurry preparation tank 85 and within the systems communicated with this beforehand, the oxygen within the same systems and within the slurry is replaced with the inert gas, and the purging step is finished.

Next, the pressure equalizing line on-off valve 88*a* of the pressure equalizing line 88 is opened, and by communicating the gas phase part 83 (upper part void part) in the reactor 30 and the upper part void part in the slurry preparation tank 85, the pressures inside the reactor 30 and the slurry preparation tank 85 are adjusted to the same (pressure equalization step).

Next, the upper part communication line on-off valve 86*a* of the upper part communication line 86 and the lower part communication line on-off valve 87*a* of the lower part communication line 87 are opened. Then, a portion of the slurry S in the reactor 30, as a result of its own weight, flows down through the upper part communication line 86 in the inclination direction thereof, and is directed to the slurry preparation tank 85. Furthermore, a portion of the slurry S in the slurry preparation tank 85, as a result of its own weight, flows down through the lower part communication line 87 in the inclination direction thereof, and is directed into the reactor 30. Consequently, the slurry S in the reactor 30 and the slurry S in the slurry preparation tank 85 are circulated (slurry circulation step) via the upper part communication line 86 and the lower part communication line 87.

At this time, as mentioned above, since the upper part communication line 86 and the lower part communication line 87 are respectively inclined at an inclination angle of approximately 45 degrees, the slurry S flowing within the upper part communication line 86 and the lower part communication line 87 smoothly flows down along the incline without the catalyst particles settling and remaining on the inner surface of the line.

Furthermore, since stationary operation of the reactor 30 is continued at that time, the slurry S introduced from the slurry preparation tank 85 to the lower part (bottom part) side of the reactor 30, that is, the slurry S in which fresh catalyst is suspended, rises in the reactor 30 by the synthesis gas introduced from the supply line 41. Consequently, the fresh catalyst accompanying the upward flow of the slurry S contributes to the FT synthesis reaction of synthesis gas, and gradually raises the carbon monoxide conversion rate mentioned above.

In the slurry circulation step, the height (level) of the liquid surface L of the slurry S in the reactor 30 does not rapidly change, and is maintained in a state in which it is mostly stable. Furthermore, since the slurry S in the slurry preparation tank 85 is naturally directed to the reactor 30 by its own weight without pressure transfer by the inert gas, a conventional blow-out of gas does not occur.

Therefore, when an additional filling (additional charging) of fresh catalyst by this slurry circulation is performed, by lowering the reaction temperature of the reactor 30 to an extent anticipating fresh catalyst charging for example, stationary operation can be continuously performed. That is, it is not necessary to excessively lower the temperature in advance, and mechanical loss can be suppressed to a minimum.

By continuing the slurry circulation step, the catalyst in the reactor 30 is replaced with fresh catalyst, and accordingly, the carbon monoxide conversion rate mentioned above rises. When the carbon monoxide conversion rate rises to a preset value, or the rising stops, in addition to closing the upper part communication line on-off valve 86a of the upper part communication line 86, the pressure equalizing line on-off valve 88a of the pressure equalizing line 88 is closed. Next, the on-off valve 91a of the inert gas introduction line 91 is opened, and the inert gas is introduced to the slurry preparation tank 85. Consequently, the slurry S in the slurry preparation tank 85 is introduced from the lower part communication line 87 into the reactor 30.

At that time, since the slurry S containing fresh catalyst charged into the slurry preparation tank 85 is already mostly transported into the reactor 30 and circulated therein in the slurry circulation step, stationary operation is continued in the reactor 30. Consequently, the inert gas introduced to the slurry preparation tank 85 is gradually introduced at a flow rate that is the necessary minimum, and the slurry S remaining in the slurry preparation tank 85 can be gradually pressure-transferred into the reactor 30. That is, in order to avoid rapid changes in the height (level) of the liquid surface L of the slurry S in the reactor 30 as a result of the slurry S that is pressure-transferred from the slurry preparation tank 85, the introduction amount of the inert gas can be controlled to match the draw-out speed of the heavy oil, which is drawn out from the reactor 30.

When the slurry S remaining in the slurry preparation tank 85 and the lower part communication line 87 is completely pressure-transferred into the reactor 30 in this manner, the lower part communication line on-off valve 87a is closed, and further, the on-off valve of the inert gas introduction line 91 is also closed (slurry circulation completion step), and the catalyst filling method of the present embodiment is completed.

Consequently, fresh catalyst can be additionally filled (charged) in a state where the reactor 30 is in stationary operation, without the inert gas introduced to the slurry preparation tank 85 blowing through the reactor 30 and generating inconveniences, such as changes in the operation conditions, including the temperature or the pressure of the reactor 30, or rapid fluctuations in fluid state of the slurry.

The liquid hydrocarbons synthesized by the reactor 30 in the above manner are introduced as a slurry together with the catalyst particles to the catalyst separator 36 as shown in FIG. 1.

The catalyst separator 36 separates the slurry into a solid component, such as the catalyst particles, and a liquid component containing the liquid hydrocarbons. The separated solid component, such as the catalyst particles, has a portion thereof returned to the reactor 30, and the liquid component is supplied to the first fractionator 40.

Furthermore, from the tower top of the reactor 30, the FT gas component containing the unreacted synthesis gas (feedstock gas) and the gas component of the synthesized hydrocarbons is discharged and supplied to the vapor-liquid separator 38.

The vapor-liquid separator 38 cools the FT gas component, separates the liquid hydrocarbons (light FT hydrocarbons) of the condensate, which is one portion, and introduces it to the first fractionator 40. On the other hand, the gas component separated at the vapor-liquid separator 38 has unreacted synthesis gas (CO and $H_2$) and hydrocarbons with two or less carbon atoms as the primary components, and a portion is charged again into the bottom part of the reactor 30 via the first recirculation path 45 and recycled to the FT synthesis reaction. Furthermore, the gas component that is not recycled to the FT synthesis reaction is discharged to the off-gas side, and is utilized as a fuel gas, or the fuel corresponding to LPG (liquid petroleum gas) is recovered, or it is recycled as a feedstock of the reformer 12 of the synthesis gas production unit 3.

Next, the first fractionator 40 fractionally distills the liquid hydrocarbons supplied from the bubble column reactor 30 via the catalyst separator 36 and the vapor-liquid separator 38 in the above manner, and separates them into a naptha fraction (boiling point lower than approximately 150° C.), a middle distillate (boiling point of approximately 150 to 360° C.), and a wax fraction (boiling point exceeding 360° C.).

The liquid hydrocarbons of the wax fraction (primarily $C_{21}$ and above) taken out from the bottom part of the first fractionator 40 are transported to the wax fraction hydrocracking reactor 50, the liquid hydrocarbons of the middle distillate (primarily $C_{11}$ to $C_{20}$) taken out from the middle part of the first fractionator 40 are transported to the middle distillate hydrotreating reactor 52, and the liquid hydrocarbons of the naphtha fraction (primarily $C_5$ to CO taken out from the upper part of the first fractionator 40 are transported to the naphtha fraction hydrotreating reactor 54.

The wax fraction hydrocracking reactor 50 reduces the liquid hydrocarbons of the wax fraction (generally $C_{21}$ and above) supplied from the tower bottom of the first fractionator 40, which have a large number of carbon atoms, to a number of carbon atoms thereof of $C_{20}$ and below by hydrocracking utilizing hydrogen gas supplied from the hydrogen separator 26. In this hydrocracking reaction, the C—C bonds of hydrocarbons with a large number of carbon atoms are broken by utilizing a catalyst and heat, and low-molecular-weight hydrocarbons with a small number of carbon atoms are generated. By this wax fraction hydrocracking reactor 50, the product, which contains liquid hydrocarbons in which hydrocracking has been performed, is separated into a gas and a liquid in the vapor-liquid separator 56, and of these, the liquid hydrocarbons are transported to the second fractionator 70, and the gaseous component (including hydrogen gas) is transported to the middle distillate hydrotreating reactor 52 and the naphtha fraction hydrotreating reactor 54.

The middle distillate hydrotreating reactor 52 performs hydrorefining of the liquid hydrocarbons of the middle distillate (generally $C_{11}$ to $C_{20}$) supplied from the middle part of the first fractionator 40, which have an intermediate number of carbon atoms, by using the hydrogen gas supplied from the hydrogen separator 26 via the wax fraction hydrocracking reactor 50. In this hydrorefining reaction, primarily, with an object of improving the low-temperature flowability as a fuel oil base stock, the liquid hydrocarbons are hydroisomerized in order to obtain branched saturated hydrocarbons, and furthermore, the unsaturated hydrocarbons contained within the liquid hydrocarbons are saturated by the addition of hydrogen. Moreover, the oxygen-containing compounds, such as alcohols, contained within the hydrocarbons are hydrogenated and converted to saturated hydrocarbons. In this manner, the product, which contains liquid hydrocarbons in which hydrorefining has been performed, is separated into a gas and a liquid in the vapor-liquid separator 58, and among these, the liquid hydrocarbons are transported to the second fractionator 70, and the gaseous component (including hydrogen gas) is recycled to the hydrogenation reaction.

The naphtha fraction hydrotreating reactor 54 performs hydrorefining of the liquid hydrocarbons of the naphtha fraction (generally $C_{10}$ and below) supplied from the upper part of the first fractionator 40, which have a small number of carbon atoms, by using the hydrogen gas supplied from the hydrogen separator 26 via the wax fraction hydrocracking reactor 50. Consequently, the unsaturated hydrocarbons and the oxygen-containing compounds, such as alcohols, contained in the supplied naphtha fraction are converted to saturated hydrocarbons. In this manner, the product, which contains liquid hydrocarbons in which hydrorefining has been performed, is separated into a gas and a liquid in the vapor-liquid separator 60, and among these, the liquid hydrocarbons are transported to the naphtha stabilizer 72, and the gaseous component (including hydrogen gas) is recycled to the hydrogenation reaction.

Next, the second fractionator 70, in the manner mentioned above, fractionally distills the liquid hydrocarbons in which hydrocracking and hydrorefining have been respectively performed in the wax fraction hydrocracking reactor 50 and the middle distillate hydrotreating reactor 52, into hydrocarbons in which the number of carbon atoms is $C_{10}$ or less (boiling point is lower than approximately 150° C.), a kerosene fraction (boiling point of approximately 150 to 250° C.), a gas oil fraction (boiling point of approximately 250 to 360° C.), and an uncracked wax fraction (boiling point exceeding approximately 360° C.) from the wax fraction hydrocracking reactor 50. The gas oil fraction is taken out from the lower part of the second fractionator 70, and the kerosene fraction is taken out from the middle part. On the other hand, the hydrocarbons with a number of carbon atoms of $C_{10}$ and below are taken out from the tower top of the second fractionator 70 and supplied to the naphtha stabilizer 72.

Furthermore, in the naphtha stabilizer 72, the hydrocarbons with a number of carbon atoms of $C_{10}$ and below supplied from the naphtha fraction hydrotreating reactor 54 and the second fractionator 70 are distilled, and naphtha ($C_5$ to $C_{10}$) is separated and purified as a finished product. Consequently, high-purity naphtha is taken out from the tower bottom of the naphtha stabilizer 72. On the other hand, from the tower top of the naphtha stabilizer 72, the gas having as the primary components hydrocarbons with a predetermined number of carbon atoms or less ($C_4$ and below), which are excluded from the finished product, is recovered as a fuel gas or discharged as a flare gas.

According to the catalyst filling apparatus 84 of a bubble column slurry bed reactor, and the catalyst filling method of a bubble column slurry bed reactor using this catalyst filling apparatus 84 of the present embodiment, the slurry preparation tank 85 is provided adjacent to the reactor 30. Therefore, by communicating the gas phase part 83 (upper part void part) in the reactor 30 with the upper part void part in the slurry preparation tank 85 via the pressure equalizing line 88 and making the pressures inside the reactor 30 and the slurry preparation tank 85 the same, along with communicating the upper part of the reactor 30 with the upper part of the slurry preparation tank 85 in that state via the upper part communication line 86, and communicating the lower part of the reactor 30 with the lower part of the slurry preparation tank 85 via the lower part communication line 87, the slurry S can be circulated between the reactor 30 and the slurry preparation tank 85 by its own weight. Further, the slurry with fresh catalyst can be rapidly charged into the reactor 30 without the lines and the like blocking as a result of the catalyst within the slurry settling and separating.

Therefore, from a state in which the slurry S is circulated in this manner, by closing the pressure equalizing line 88 and closing the upper part communication line 86, and by introducing the inert gas to the slurry preparation tank 85 in that state, the slurry S in the slurry preparation tank 85 can be completely pressure-transferred from the lower part communication line 87 into the reactor 30. At that time, the slurry S containing fresh catalyst in the slurry preparation tank 85 is already circulated and transported into the reactor 30, and consequently, stationary operation is performed in the reactor 30. Therefore, the inert gas introduced to the slurry preparation tank 85 is gradually introduced at a flow rate that is the necessary minimum, and the slurry remaining in the slurry preparation tank 85 can be gradually pressure-transferred into the reactor 30. As a result, inconveniences, such as the inert gas introduced to the slurry preparation tank 85 blowing through the reactor 30 and changing the operation conditions, such as the temperature and the pressure of the reactor 30, or rapidly changing the fluid state of the slurry, can be prevented.

Therefore, with respect to the operation of the bubble column slurry bed reactor, fresh catalyst can be filled into the reactor while stably continuing stationary operation without changing the course of the FT synthesis reaction to a significantly inhibited operation condition, or temporarily stopping the operation. Furthermore, since fresh catalyst can be introduced during stationary operation, an exceptional effect can be achieved in which losses in mechanical loss, operation time, operation costs, and the like, can be avoided.

The foregoing has described in detail an embodiment of the present invention with reference to the drawings. However the specific configuration is in no way limited to this embodiment, and design changes and the like are included within a scope that does not depart from the gist of the present invention.

For example, in the embodiment, a case in which fresh FT synthesis reaction catalyst is filled into the bubble column slurry bed reactor 30 by the catalyst filling apparatus 84 was described. However, it may be made such that prior to this, a portion of the catalyst in the bubble column slurry bed reactor 30 in which the activity has decreased is drawn out from the bubble column slurry bed reactor 30, and fresh FT synthesis reaction catalyst is filled into the bubble column slurry bed reactor 30 thereafter by the catalyst filling apparatus 84. That is, the catalyst filling apparatus of the bubble column slurry bed reactor and the catalyst filling method according to the present invention can be applied not only to a case where fresh FT synthesis reaction catalyst is filled into the bubble column slurry bed reactor 30, but also a case where the FT synthesis reaction catalyst in the bubble column slurry bed reactor 30 is exchanged for fresh FT synthesis reaction catalyst.

INDUSTRIAL APPLICABILITY

The present invention can be utilized for a catalyst filling apparatus of a bubble column slurry bed reactor that produces hydrocarbons by the Fischer-Tropsch synthesis reaction, and a catalyst filling method of a bubble column slurry bed reactor using this catalyst filling apparatus.

BRIEF DESCRIPTION OF THE REFERENCE SYMBOLS

1 LIQUID FUEL SYNTHESIS SYSTEM
5 FT SYNTHESIS UNIT
30 BUBBLE COLUMN SLURRY BED REACTOR (REACTOR)
80 REACTOR BODY
84 CATALYST FILLING APPARATUS
85 SLURRY PREPARATION TANK
86 UPPER PART COMMUNICATION LINE
86A UPPER PART COMMUNICATION LINE ON-OFF VALVE

87 LOWER PART COMMUNICATION LINE
87A LOWER PART COMMUNICATION LINE ON-OFF VALVE
88 PRESSURE EQUALIZING LINE
88A PRESSURE EQUALIZING LINE ON-OFF VALVE
89 CATALYST CHARGING INLET
90 SLURRY PREPARATION OIL SUPPLY LINE
90A ON-OFF VALVE
91 INERT GAS INTRODUCTION LINE
91A ON-OFF VALVE
92 INERT GAS SOURCE
93 HEATING TUBE
94 STIRRER
95 VENT LINE
95A VENT VALVE
96 LIQUID SURFACE MEASUREMENT DEVICE
S SLURRY
L LIQUID SURFACE
H LIQUID LAYER HEIGHT

The invention claimed is:

1. A catalyst filling apparatus provided in a bubble column slurry bed reactor for a Fischer-Tropsch synthesis reaction, the catalyst filling apparatus comprising:
    a slurry preparation tank installed adjacent to the reactor, and configured to prepare a slurry from a Fischer-Tropsch synthesis reaction catalyst and a slurry preparation oil;
    an upper part communication line configured to direct the slurry in the reactor to the slurry preparation tank;
    an upper part communication line on-off valve provided on the upper part communication line;
    a lower part communication line configured to direct the slurry in the slurry preparation tank to the reactor;
    a lower part communication line on-off valve provided on the lower part communication line;
    a pressure equalizing line configured to communicate an upper part void part in the reactor with an upper part void part in the slurry preparation tank and to make the pressures inside the reactor and the slurry preparation tank the same; and
    a pressure equalizing line on-off valve provided on the pressure equalizing line,
    wherein the upper part communication line is connected to the reactor in a position that, with respect to the slurry liquid in the reactor during stationary operation, is equal to or higher than a half level of the slurry liquid in a height direction of the reactor and is lower than a liquid surface of the slurry,
    the upper part communication line is downwardly inclined from the reactor toward the slurry preparation tank, and is connected to the slurry preparation tank in a position that is equal to or higher than a half level of the slurry preparation tank in a height direction of the slurry preparation tank,
    the lower part communication line is connected to the reactor in a position that, with respect to the slurry liquid in the reactor during stationary operation, is lower than the half level of the slurry liquid in the height direction of the reactor,
    the lower part communication line is upwardly inclined from the reactor toward the slurry preparation tank, and is connected to the slurry preparation tank in a position that is the lower end section of the slurry preparation tank, and
    the slurry preparation tank is provided with a catalyst charging device configured to charge a Fischer-Tropsch synthesis reaction catalyst, an inert gas introducing device configured to introduce an inert gas to the slurry preparation tank, a slurry preparation oil supplying device configured to supply a slurry preparation oil, a slurry heating device that heats the slurry in the slurry preparation tank, and a slurry stirring device configured to stir the slurry to mix the slurry.

2. A catalyst filling method of a bubble column slurry bed reactor for filling a Fischer-Tropsch synthesis reaction catalyst into a bubble column slurry bed reactor for a Fischer-Tropsch synthesis reaction using the catalyst filling apparatus of a bubble column slurry bed reactor according to claim 1, the catalyst filling method comprising:
    a slurry preparation step of stirring a slurry preparation oil in the slurry preparation tank on heating to make a prepared slurry in which the catalyst is suspended within the slurry preparation oil;
    a purging step in which an inert gas is introduced to the slurry preparation tank by the inert gas introducing device to replace oxygen within the prepared slurry and the slurry preparation tank with inert gas;
    a pressure equalization step after the purging step, in which the pressure equalizing line on-off valve is opened to make the pressures inside the reactor and the slurry preparation tank the same;
    a slurry circulation step after the pressure equalization step, in which the slurry in the slurry preparation tank is introduced to the reactor while introducing the slurry in the reactor to the slurry preparation tank by opening the upper part communication line on-off valve and the lower part communication line on-off valve, and
    a slurry circulation completion step following the slurry circulation step, in which the upper part communication line on-off valve and closing the pressure equalizing line on-off valve are closed, subsequently the inert gas is introduced to the slurry preparation tank by the inert gas introducing device to pressure transfer the slurry in the slurry preparation tank via the lower part communication line to the reactor, and thereafter the lower part communication line on-off valve is closed.

* * * * *